United States Patent
LaMontagne (10) Patent No.: US 10,801,079 B2
(45) Date of Patent: Oct. 13, 2020

(54) GNOTOBIOTIC RHIZOBACTERIAL ISOLATION PLANT SYSTEMS AND METHODS OF USE THEREOF

(71) Applicant: University of Houston System, Houston, TX (US)

(72) Inventor: Michael LaMontagne, League City, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 16/300,103

(22) PCT Filed: May 9, 2017

(86) PCT No.: PCT/US2017/031763
§ 371 (c)(1),
(2) Date: Nov. 9, 2018

(87) PCT Pub. No.: WO2017/196850
PCT Pub. Date: Nov. 16, 2017

(65) Prior Publication Data
US 2019/0144952 A1    May 16, 2019

Related U.S. Application Data

(60) Provisional application No. 62/333,487, filed on May 9, 2016.

(51) Int. Cl.
*C12Q 1/04* (2006.01)
*G16B 30/00* (2019.01)
*C12N 1/20* (2006.01)
*G16B 50/30* (2019.01)
*C12R 1/07* (2006.01)
*C12Q 1/689* (2018.01)
*C40B 40/02* (2006.01)

(52) U.S. Cl.
CPC .................. *C12R 1/07* (2013.01); *C12N 1/20* (2013.01); *C12Q 1/04* (2013.01); *C12Q 1/689* (2013.01); *G16B 30/00* (2019.02); *G16B 50/30* (2019.02); *C40B 40/02* (2013.01); *G01N 2333/32* (2013.01)

(58) Field of Classification Search
None
See application file for complete search history.

(56) References Cited

U.S. PATENT DOCUMENTS 9,615,584 B2 *   4/2017   Reddy .................... C12R 1/885

* cited by examiner

*Primary Examiner* — Padmavathi Baskar
(74) *Attorney, Agent, or Firm* — Jackson Walker LLP (57) ABSTRACT

The invention provides methods of enriching and isolating novel microbial organisms, such as rhizobacteria, that promote the growth of plants by recreating the rhizosphere in a laboratory setting. The methods of the invention can be used to produce and characterize beneficial microbes grown at the root-soil interface and provide a technique for selectively enriching bacteria that live in close association with plants and foster the growth thereof.

22 Claims, 4 Drawing Sheets

Cluster dendrogram with AU/BP values %

GNOTOBIOTIC RHIZOBACTERIAL ISOLATION PLANT SYSTEMS AND METHODS OF USE THEREOF

This application claims priority to PCT Application No. PCT/US17/31763, filed on May 9, 2017 which claims priority to U.S. Provisional Patent Application No. 62/333,487 filed on May 9, 2016, which is specifically incorporated by reference in its entirety herein.

FIELD OF THE INVENTION

The invention relates to methods for the enrichment and isolation of beneficial and previously uncharacterized microorganisms from the rhizosphere for agricultural and biotechnological applications.

BACKGROUND OF THE INVENTION

Discovery of novel microbes, and the natural products they generate, can address three important challenges: the corning food crisis, climate change, and the end of the antibiotics era. Current agricultural practices on available arable land will not meet the nutritional needs of a population that will reach nine billion people by the middle of this century. Microbial products can help by increasing the yield and sustainability of agricultural systems (31), particularly on marginal lands. Increasing the incorporation of microbial products into agricultural practice will also benefit the climate by allowing growers to use less synthetic fertilizers, decreasing the release of greenhouse gases from fields, and increasing the production of biofuel crops (15). These libraries of microbes, and the metabolites they generate, will also provide a resource for programs that seek to discover desperately needed novel antibiotics. Soils contain a deep, diverse reservoir of beneficial microbes that can supply our need for a new generation of microbial products. However, available techniques limit our ability to bioprospect soils for microbial discovery. Only a fraction of soil microbes grow on standard laboratory media.

The percentage of microbes in a system that can be recovered using standard techniques varies between sources. Recoveries as high as 40% of viable cells from a gut microbiome have recently been reported (23); however, isolation from soil presents a particular challenge. Recoveries of 7% from soil, using standard techniques, require dilute media and long incubation times (10). Soil microbes often form particle-associated communities, which are difficult to replicate in the laboratory. In communities, microbes produce different secondary metabolites (36). Slow-growing microbes may require these metabolites as signal molecules. Additionally, soils contain slow- and fast-growing microbes, and fast growers tend to outcompete slow growers in enrichments and can overrun slower-growing isolates on plates.

Recent developments have dramatically increased recovery rates from bulk soils. In situ cultivation approaches address the challenge of providing the appropriate media and signal molecules by incubating microbes in diffusion chambers deployed in their native environments (12). A related approach involves co-culture with "helper" microbes that release signal molecules and metabolites that supports the growth of fastidious microbes (29). Progress in growth media development includes the generation of databases that facilitate prediction of effective formulations from metagenomic data (21, 24, 37), as well as improvements to reduce the toxicity of media components (30). Alternative gelling agents have also been incorporated into growth media (6), such as by the substitution of gellan gum for agar (10, 20). Coupling of multiple media formulations to MALDI-TOF-enabled high throughput microbial identification has also shown significant potential for increasing microbial discovery rates (16).

Efficient development of microbial products for agriculture requires methods to recover microbes from the rhizosphere, where microbes form close associations with plant roots. This root microbiome is rich in the beneficial microbial symbionts, plant growth-promoting rhizobacteria (PGPR), and microbes with value for antibiotic and other drug discovery. PGPR can also help plants tolerate drought conditions, as well as poor and contaminated soils (5). Climate change will increase extreme weather events, including drought, that threaten our food supply. In parallel, continued urbanization of farmland gradually eliminates arable land (28). PGPR products can help build a more stable, productive, and sustainable agricultural sector of the economy. PGPR are, by definition, symbionts. The association of these bacteria with plants represents a life strategy that produces bioactive compounds (18). Animal symbionts are also targeted for drug discovery programs (13) and algal epiphytic communities are rich in microbes that produce antimicrobials (34). Recently, several groups have developed methods to culture symbionts from animals. These approaches include the use of the iTip, which improves recovery of symbionts associates with sponges (11) and the use of gnotobiotic animals to recover microbes from the gut microbiome (8). The root microbiome is particularly rich in microbes that produce antimicrobials and other potentially valuable natural products (4, 14, 22). There remains a need for methods to enrich, recover, and characterize these beneficial microbes.

Discovery of novel PGPR is limited by the fact that most soil bacteria do not readily grow in the laboratory and the commonly used approaches of microbial identification by DNA sequencing are expensive. Given these challenges, the plant root microbiome remains a poorly described "black box," with few representative isolates. Further, evaluation of prospects by greenhouse trials is very expensive and fraught with biases. Greenhouse studies do not appear reproducible or necessarily predictive of performance in the field.

SUMMARY OF THE INVENTION

An embodiment of the disclosure is a method of isolating one or more microbial organisms, the method comprising: contacting an inoculum comprising the one or more microbial organisms with a surface-sterilized seed; incubating the surface-sterilized seed in a sterilized growth medium under aseptic conditions suitable for the growth of a seedling; and isolating the one or more microbial organisms from the growth medium. In an embodiment, the growth medium has been sterilized by autoclaving, fumigation, or exposure to gamma radiation. In an embodiment, the growth medium comprises soil. In an embodiment, the soil is field soil or artificial soil. In an embodiment, the growth medium further comprises sand. In an embodiment, the growth medium is maintained in a round-bottom or cylindrical glass tube. In an embodiment, the one or more microbial organisms comprise a bacterium. In an embodiment, the bacterium is selected from the group consisting of unclassified Bacilli, *Naxibacter, Bacillus,* unclassified Geobacilli, *Tumebacillus, Paenibacillus, Chitinophaga, Methylobacterium,* and *Sphingopyxis.* In an embodiment, the bacterium is a *Bacillus.* In an embodiment, the surface of the seed has been sterilized by contacting the surface with ethanol. In an embodiment, the inoculum comprises a limiting quantity of the microbial organisms sufficient to permit inoculation of the seed with the microbial organism. In an embodiment, the inoculum comprises a sample obtained from the rhizosphere, rhizoplane, or endosphere of a plant. In an embodiment, the inoculum comprises soil and water. In an embodiment, wherein the inoculum is obtained by mixing soil comprising a homogeneous or heterogeneous population of microbial organisms and water to form a suspension. In an embodiment, the method further comprising diluting the suspension. In an embodiment, the suspension is diluted by a factor of from 10 to 100,000 in water. In an embodiment, the method further comprising exposing the inoculum to heat or ethanol. In an embodiment, the method further comprising adding water to the growth medium during the incubating. In an embodiment, the method further comprising contacting the growth medium with one or more antibiotics during the incubating. In an embodiment, the method further comprising contacting the growth medium with one of more selected from the group consisting of chitin, 1-aminocyclopropane-1-carboxylic acid, and insoluble phosphate. In an embodiment, the method further comprising maintaining the seedling within the growth medium for about 2 weeks following germination of the seedling. In an embodiment, the seedling is exposed to alternating light/dark cycles while maintained within the growth medium. In an embodiment, the one or more microbial organisms are isolated from a root of the seedling. In an embodiment, the one or more microbial organisms are isolated from the root of the seedling by: mixing the root with water; separating the mixture formed in step (a) by centrifugation; and inoculating a culture medium with a pellet produced in step (b). In an embodiment, the method further comprising maintaining the culture medium under conditions suitable for the growth of the one or more microbial organisms.

An embodiment of the disclosure is a method of generating a library of microbial isolates, the method comprising: isolating a microbial organism; determining the polynucleotide sequence of one or more regions of the genome of the microbial organism; and storing the polynucleotide sequence in a database. In an embodiment, the one or more regions of the genome of the microbial organism comprise an rRNA gene.

An embodiment of the disclosure is a method of generating a symbiotic relationship between a microbial organism and a plant, the method comprising isolating a microbial organism and culturing the plant in the presence of the microbial organism. In an embodiment, the microbial organism is a *Bacillus* bacterium. In an embodiment, the plant is maize, cotton, a soybean, or wheat, a wild relative of one or more of these plants, or a model plant widely used in agricultural research, preferably wherein the model plant is *Arabidopsis, Brachypodium*, or *Medicago*.

An embodiment of the disclosure is a database comprising a library of microbial isolates.

The invention provides methods of isolating and characterizing previously unknown microbial organisms by efficiently culturing and recovering microbes through the use of a gnotobiotic rhizobacterial isolation plant system (GRIPS). A GRIPS contains seedlings grown from surface-sterilized seeds using aseptic techniques. By inoculating GRIPS with microbes, the system supports the growth of unique microbes that form close relationships with a plant host.

In a first aspect, the invention features a method of isolating one or more microbial organisms by contacting an inoculum that contains the one or more microbial organisms with a surface-sterilized seed. The surface-sterilized seed is then incubated in a growth medium, e.g., under conditions suitable for the growth of a seedling, and the microbial organisms are subsequently isolated from the growth medium or the seedling. Media used to grow plants in the system may involve combinations of soil, potting mix, sand, perlite, and compost. The surface of the seed may be sterilized by contacting the surface with a sterilizing agent, such as bleach, ethanol, or by fumigation with gasses such as phosphine or methyl bromide.

In some embodiments, the growth medium is sterilized. For instance, the growth medium may be sterilized by autoclaving, fumigation, or by exposure to gamma radiation. In some embodiments, the growth medium contains soil, such as field soil or artificial soil, and/or sand. The growth medium may be maintained in a container, e.g., in a round-bottom or cylindrical glass tube.

In some embodiments, the one or more microbial organisms include a bacterium, such as unclassified Bacilli, *Naxibacter, Bacillus*, unclassified Geobacilli, *Tumebacillus, Paenibacillus, Chitinophaga, Methylobacterium*, or *Sphingopyxis*.

In some embodiments, the inoculum contains a limiting quantity of the microbial organisms that is sufficient to permit inoculation of the seed with the microbial organism. The inoculum may contain a sample obtained from the rhizosphere, rhizoplane, or endosphere of a plant. The inoculum may contain soil and water. For instance, the inoculum may be obtained by mixing soil containing a homogeneous or heterogeneous population of microbes and a liquid, such as water, to form a suspension, and, for example, subsequently diluting the suspension in the liquid (e.g., by a factor of from 10 to 100,000, such as by a factor of 10, 100, 1,000, 10,000, or 100,000). Liquid used to dilute the inoculum may include salts and buffers, such as various formulations of phosphate buffered saline solutions designed to minimize osmotic stress on the inoculum or to disassociate microbes from particles. In some embodiments, the method includes exposing the inoculum to heat and/or ethanol, e.g., to select for or against the growth of certain microbial organisms.

In some embodiments, the method includes adding water to the growth medium after incubating the seed in the growth medium. The method may include adding one or more antibiotics to the growth medium during the incubation period, e.g., to select for or against the growth of certain microbial organisms. Examples of this approach include supplementing the growth medium with nystatin, actidione, polymyxin, or penicillin, e.g., to select for actinomyceters (38) or cyclohexamide, e.g., to select against fungi (39). In some embodiments, organic nitrogen is utilized as the nitrogen source. In some embodiments, nitrogen-free media is utilized to select for nitrogen fixing microbes. In some embodiments, the method includes maintaining the seedling within the growth medium, e.g., for from about 1 day to about 2 months (e.g., about 1 day, 2 days, 3 days, 4 days, 5 days, 6 days, 7 days, 2 weeks, 3 weeks, 4 weeks, 5 weeks, 6 weeks, 7 weeks, 8 weeks, or longer) following germination of the seedling. In some embodiments, the seedling is exposed to alternating light/dark cycles while maintained within the growth medium. For instance, a preferred light/dark cycle includes 16 hours of exposure to light alternating with 8 hours of darkness.

The one or more microbial organisms may be isolated from a root of the seedling. For instance, the one or more microbial organisms may be isolated from the root by mixing the root with water, separating the ensuing mixture by centrifugation, and inoculating a culture medium with a pellet produced by the centrifugation. For instance, a culture medium, such as a bacterial growth medium, may be inoculated with a microbial organism thus separated from a root of the seedling, and the culture medium may subsequently be maintained under conditions suitable for the growth of the microbial organism. In this way, the microbial organism can be isolated and amplified.

In some embodiments, the method includes characterizing the one or more microbial organisms (e.g., bacteria) by determining the nucleic acid sequence of a region of the genome of the microbial organism. For instance, the method may include characterizing the microbial organism by determining the nucleic acid sequence of a ribosomal RNA (rRNA) gene of the microbial organism, the 16S rRNA gene, other ribosomal genes, or other genes widely used for phylogenetic studies, such as recA, rpoB, gyrB and other so-called housekeeping genes widely used to characterize microbial isolates (40, 41). This may be performed, e.g., by amplifying the microbial rRNA gene (for instance, using a polymerase chain reaction (PCR) technique) and subsequently determining the nucleic acid sequence of the microbial rRNA gene or by sequencing the whole genome.

In another aspect, the invention provides a method of generating a library of microbial isolates by isolating a microbial organism according to any of the above embodiments of the invention, determining the polynucleotide sequence of one or more regions of the genome of the microbial organism, and creating and/or storing the polynucleotide sequence in a database. For instance, the one or more regions of the genome may include an rRNA gene, such as a 16S rRNA gene. The microbial organism thus catalogued may be a previously unknown or uncharacterized organism, e.g., as determined by comparing a polynucleotide sequence of the microbial organism to similar sequences, e.g., from a database(s) containing sequences of an analogous region(s) of the genome(s) of the other microbe(s).

In another aspect, the invention features a method of generating a symbiotic relationship between a microbial organism and a plant by isolating a microbial organism by the method of any of the above embodiments of the invention and subsequently culturing the plant in the presence of the microbial organism. This can be done, e.g., by inoculating a seed that gives rise to the plant with a mixture containing the microbial organism and subsequently incubating the seed in a growth medium. Additionally or alternatively, the beneficial microbial organism can be introduced directly into the growth medium while the seed or plant is incubating in the growth medium, e.g., by contacting the growth medium with a mixture containing the microbial organism. In some embodiments, the microbial organism is a *Bacillus* bacterium. In some embodiments, the plant may be a commercially valuable crop (e.g., maize, soybeans, cotton, or wheat), the wild relatives of these plants, or, in some embodiments, genera of plants widely used in agricultural research (e.g., *Arabidopsis, Brachypodium*, or *Medicago*).

In another aspect, the invention features a library of microbial isolates obtained by the method of any of the above embodiments of the invention.

In yet another aspect, the invention features an isolated microbe prepared by the method of any of the above embodiments of the invention. In some embodiments, the isolated microbe is admixed with a seed or a plant, such as maize or wheat.

The invention also features a composition that includes the isolated an isolated microbe prepared by the method of any of the above embodiments of the invention. In some embodiments, the composition includes a seed or a plant, such as maize or wheat.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope, the disclosure will be described with additional specificity and detail through the use of the accompanying drawings in which.

DETAILED DESCRIPTION

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings making apparent to those skilled in the art how the several forms of the disclosure may be embodied in practice.

The following explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary 3rd Edition.

Microbial products can mitigate the coming food crisis by increasing crop yield [31] and helping crops tolerate drought and marginal soils [5].

Different soils and crops will require optimized formulations, but little is known about pairing microbes with soil type or specific crop genotypes. In an embodiment, soil tests can be used to inform growers of not just their fertilizer needs but their microbial needs as well. Libraries will be developed that allow development of custom formulations. Value will be added to this portfolio by cataloging secondary metabolites produced by our isolates.

Gnotobiotic Rhizobacteria Isolation Plant System (GRIPS) recovers beneficial bacteria that form close associations with plant roots by growing microbes in an environment that mimics their niche. This system recovers valuable PGPR and reduces the complexity of the plant microbiome to facilitate metagenomic analysis.

The growing library of microbes isolated, and the gnotobiotic systems developed, will facilitate fundamental, and potentially transformative, research in plant-microbe interactions. Mapping the plant microbiome will provide the framework for this program. The human microbiome project has led to rapid increases in our understanding of human health [135]. Parallels exist in the relationship between the root microbiome and plant health [82]. For example, the diversity of soil microbes correlates with the primary productivity of grasslands [152] and soil functioning [96]. This has led to theories as to the factors controlling bacterial diversity in soil systems [57]; however, the paucity of representative isolates from soils fundamentally limits understanding of plant-microbe interactions [74, 126]. To address this challenge, the sequence of the plant microbiome will be mapped. GRIPS can accelerate this metagenomic analysis.

GRIPS selects, enriches, and isolates bacteria that form close associations with plant roots. This system produces a simplified model plant microbiome that has a tractable microbial diversity. By generating multiple systems, GRIPS disperses the diversity of the root microbiome and facilitates metagenomic analysis. GRIPS simplifies the plant microbiome and facilitated recovery of unique rhizobacteria that promote plant growth.

Gnotobiotic experiments improve the understanding of host-microbiome interactions [168] and provide a process to isolate microbes such as gut microbes [112]. This concept has been extended to isolate PGPR. GRIPS supports the growth of microbes that form close associations with plant roots. Through serial dilutions and iterative transfers, GRIPS allows for the enrichment for microbes that promote plant growth by culturing them on the rhizoplane—the interface between the plant roots and soil. The rhizobacteria is recovered by harvesting seedlings from GRIPS and isolating microbes from root samples. The iterative transfers will also help "domesticate" rhizobacteria, as described for in situ cultivation methods [12] and select for rhizobacteria that promote plant growth. Gnotobiotic systems can be utilized with the concept of using plants roots to select and enrich for PGPR.

Culturing rhizobacteria, and related microbes, presents a challenge because standard laboratory media generally do not support the growth of the vast majority of microbes associated with plant roots. This problem reflects the technical challenge of providing the metabolites released by plant hosts and microbial members of the rhizosphere that most members of the plant microbiome need to grow and the relative slow growth rate of numerically dominant rhizobacterial (19).

PGPR can help plants recover more nutrients, both applied as fertilizer or from the environment, and tolerate stressors, like drought [45]. PGPR can also control plant pathogens [46] and promote beneficial mycorrhizae colonization [15]. These interactions with plants and microbes make PGPR a rich source of secondary metabolites, such as antimicrobials and other potentially valuable natural products [14, 4, 22].

Metagenomic analysis of the root microbiome informs bioprospecting and high-throughput microbial identification by MALDI-TOF. Metagenomic analysis enables prioritization of inoculums that contain potential valuable prospects and formulate media to recover them. MALDI-TOF, when coupled to a proprietary protein spectra database, enables processing of thousands of isolates a week for pennies an isolate. Over a thousand rhizobacteria have been isolated and several strains have been identified that promote plant growth in the greenhouse.

GRIPS recovers rhizobacteria by creating a model rhizosphere in a test tube. Through serial dilutions and iterative transfers, the GRIPS allows for the enrichment for microbes that promote plant growth by culturing them on the rhizoplane—the interface between the plant roots and soil. The rhizobacteria are recovered by harvesting seedlings from GRIPS and isolating microbes from root samples.

In an embodiment, assembly of the GRIPS involves filling one or more containers, such as test tubes to approximately half their volume with growth media. For instance, round-bottom glass 25×250 mm tubes can be used, and the media may contain air-dried field soil mixed with sand (50/50). After filling with media, the tubes can then be sealed with cotton gauze or any loose-fitting cap. In an embodiment, assembled GRIPS may then be sterilized, e.g., by autoclaving, fumigation, or exposure to gamma radiation.

In an embodiment, prior to sowing seeds in GRIPS, surface-sterilized seeds can be soaked with inocula. In an embodiment, the inoculum can be generated by mixing field soil with sterile water. In an embodiment, the ensuing mixture can then be allowed to settle and subsequently serially diluted, e.g., by a factor of $10^{-5}$ in sterile water. In an embodiment, surface-sterilized seeds can then be individually soaked in one each of these dilutions (e.g., from $10^{-1}$ to $10^{-5}$) for a time sufficient to permit inoculation (e.g., 30 minutes).

In an embodiment, assembled GRIPS can then be sowed with inoculated seeds using aseptic technique. For instance, seeds inoculated with different dilutions of a soil slurry can be sown in a growth medium, e.g., a growth medium containing soil and/or sand. After sowing, using aseptic technique, the moisture content of the growth medium can be adjusted with sterile deionized water, for instance, to between about 30% and about 80% of the water holding capacity of the medium (e.g., to about 60% of the water holding capacity of the medium).

In an embodiment, sown GRIPS can then be incubated in a greenhouse or growth chamber with appropriate light/dark cycling, after one or more seedlings emerge. To recover microbes from GRIPS at harvest, root systems can be separated from adhering soil particles, e.g., by shaking. Roots can then be mixed with sterile water and the ensuing mixture can be separated by centrifugation (e.g., for 5 minutes at 8,000×g) to generate a rhizoplane pellet. The microbial (e.g., bacterial) communities in these pellets can then characterized by sequencing of gene fragments using methods known in the art, e.g., as described in reference (17), the disclosure of which is incorporated herein by reference. This sequence information can be used to generate a library of microbial isolates. From pellets obtained by centrifugation, a library of isolates can be generated by standard methods known in the art. This can involve serially diluting the inocula obtained from the plant in an appropriate buffer and plating on media suitable for microbial growth (e.g., water can be used as a buffer and dilutions can subsequently be plated on ¼ strength TSA plates). A heating step can be included in this process to select for or against particular microbes. For instance, the inocula can be heated (e.g., 65° C., 15 m) to select for the growth of spore forming bacteria.

Alternative embodiments of the invention may include other GRIPS configurations, e.g., as described below:

Alternative configurations of GRIPS include different tube shapes and sizes and different growth media. For example, instead of test tubes for the GRIPS, a cylindrical or other shaped tube can be used so long as it is sealed at both ends. This can be performed using methods known in the art, e.g., as described in reference (27), the disclosure of which is incorporated herein by reference. For the media in GRIPS, field soil can be replaced or supplemented with artificial soils (9) and/or commercially available potting mixes.

Alternative approaches to GRIPS sterilization include repeating sterilization, following a period of incubation, to eliminate endospore forming soil bacteria. Also, autoclaving can be replaced or supplemented with other sterilization techniques, including gamma radiation and fumigation (32).

Alternative approaches to treating media within GRIPS include applying antimicrobial agents, such as antibiotics, to target a particular guild in the plant microbiome. This approach would facilitate manipulation of the plant microbiome by suppressing a subset of the community, which is an effective method of testing host-microbe interactions (25). Alternative embodiments include maintaining a range of soil moisture contents, e.g., to enhance the diversity of isolates, and adjusting moisture content of the media (e.g., from 30% to 80% moisture content) with a chemically defined solution that contains nutrients, salts, and buffers designed to support the growth of particular microbes. For example, chitin could be provided as the primary carbon source in the media, e.g., to select for bacteria antagonistic to insect and fungal pests (42). The ethylene precursor 1-aminocyclopropane-1-carboxylic acid could be provided as the sole nitrogen source, e.g., to select for plant growth promoting rhizobacteria (43). Rock phosphate, or other insoluble form of phosphate, could be provided as the sole phosphate source, e.g., to select for phosphate-solubilizing microbes. In an embodiment, organic nitrogen can be utilized as the nitrogen source. In an embodiment, nitrogen-free media can be utilized to select for nitrogen fixing microbes.

In an embodiment, alternative sources of inocula for GRIPS include the rhizosphere, rhizoplane, and endosphere samples from any plant. Rhizoplane samples appear suitable for generating inocula for enrichments designed to recover PGPR (3) and for inoculate seeds (33). Endosphere samples appear suitable for recovering bacterial endophytes, particularly from roots (1). Inocula generated from the root microbiome of wild relatives of commercial crops and plants found in marginal soils would have particular value.

In an embodiment, alternative approaches of generating inocula for the GRIPS include manipulations to select for a subset of the microbiome, such as heat or ethanol treatment to select for *Bacillus*-related genera capable of forming endospores (2). Alternatively, differential centrifugation can be used to separate filamentous microbes (35).

In non-sterile soils, PGPR compete with other microbes to establish relationships with the host plant. Unfortunately, potted plant trials are fraught with biases and errors that make greenhouse experiments challenging [136]. Plants in greenhouses experience fluctuations, in light, temperature and humidity. In the field, plants face even more extreme variations. This variation could dampen, amplify or obfuscate the response of a plant to a microbial treatment. Of course, increasing replicates per treatment increases the power of an experiment, but this is labor intensive.

Dereplication by Analysis of Protein Spectra Generated by MALDI-TOF

MALDI-TOF systems provide strain-level identification of microbes [71, 26, 155], costs pennies per isolate, and has the throughput to enable the characterizing libraries of isolates with the depth and diversity that approaches metagenomic sequence libraries [16]. Commercially available protein spectra databases have poor representation of soil microbes but this should not limit the application of MALDI-TOF to environmental microbiology, as commercial software and freeware facilitate alignment and clustering of MALDI-TOF generated protein mass spectra [107, 151, 169]. These clusters, defined herein [143]. This technology accelerates microbial discovery by enabling efficient dereplication, through the identification of closely related isolates [7]. Dereplication has particular value for PGPR discovery, because of the low throughput (months) and costs ($ hundreds) of plant growth response trials.

Just as mapping the human genome and microbiome revolutionized medicine, mapping the plant microbiome, with the methods outlined herein, has the potential to revolutionize agriculture and soil science in general. Many phyla, that appear abundant in databases generated by ribosomal gene surveys of soil systems, are poorly represented in genomic databases [58]. Since so little is known about the microbes, that presumably mediate biogeochemical processes in soil, soil systems are treated as a black box. It is possible to measure fluxes of nutrients and gasses in and out of the soil but little is known about the microbes in the systems.

A pipeline will be developed that includes GRIPS and nanopore sequencing that will lead to draft genomes of several rhizobacterial species that have not been previously described. This will allow linking particular microbes with soil functions and will have broad application in ongoing efforts to develop a reference database of soil microbial genomes. The availability of draft metagenomes of rhizobacteria will allow inference of their function in the ecosystem, inform isolation strategies and lead to identification and isolation of microbes that improve agricultural yield and sustainability. The availability of draft genomes will also allow screening of genomes for pathogenicity islands, and virulence genes, using the pathogenicity island database [59]. This will protect workers and students in microbial discovery programs from the risk of accidently isolating a highly virulent strain.

EXAMPLE

The following examples are put forth so as to provide those of ordinary skill in the art with a description of how the compositions and methods described herein may be used, made, and evaluated, and is intended to be purely exemplary of the invention and is not intended to limit the scope of what the inventor regards as his invention.

Example 1. Use of GRIPS to Enrich and Analyze Rhizobacteria

This example demonstrates the application of GRIPS, packed with a media containing field soil, to isolate aerobic, spore-forming, rhizobacterial from an inoculum generated from field soil.

Prior to sowing seeds in GRIPS, surface-sterilized wheat seeds were soaked with inocula. The inoculum was generated by mixing 0.5 g of field soil with 45 ml sterile water and vortexing this slurry for a minute. This solution was allowed to settle for approximately 30 s and, using a large bore pipette and aseptic technique, was subsequently serially diluted to 10-5 in sterile water. Surface-sterilized wheat seeds were individually soaked in one each of these dilutions (10-1 to 10-5) for 30 minutes with gentle agitation every few minutes.

The wheat seeds inoculated with different dilutions of a soil slurry were then sown in a growth medium containing soil and sand. Several GRIPS controls were tested in parallel, including systems that were sown with plants that had been surface-sterilized but not inoculated. Additional controls were sown in systems containing live (not sterilized) soil. After sowing, using aseptic technique, the moisture content of the soil/sand media was brought to 60% of water holding capacity with sterile deionized water.

Sown GRIPS were then incubated in a greenhouse or growth chamber with appropriate light/dark cycling for two weeks after seedlings emerged. To recover microbes from GRIPS at harvest, root systems were separated from adhering soil particles by shaking. Roots were transferred to 50 ml conical tubes and adjusted with 10 ml of sterile water. These tubes were vortexed vigorously for 1 min, rocked at room temperature for an hour (with the tubes placed on their sides) and then centrifuged for 5 minutes (8,000×g) to generate a rhizoplane pellet. The bacterial communities in these pellets were then characterized by sequencing of PCR-amplified 16S rRNA gene fragments using methods known in the art (17), and this information was used to generate a library of microbial isolates. From pellets, a library of isolates was generated using methods known in the art. In this example, the inocula isolated from the roots as described above were serially diluted in water and subsequently plated on ¼ strength TSA plates. A heating step (65° C., 15 m) was included in this process to select for spore forming bacteria.

Figure 1:
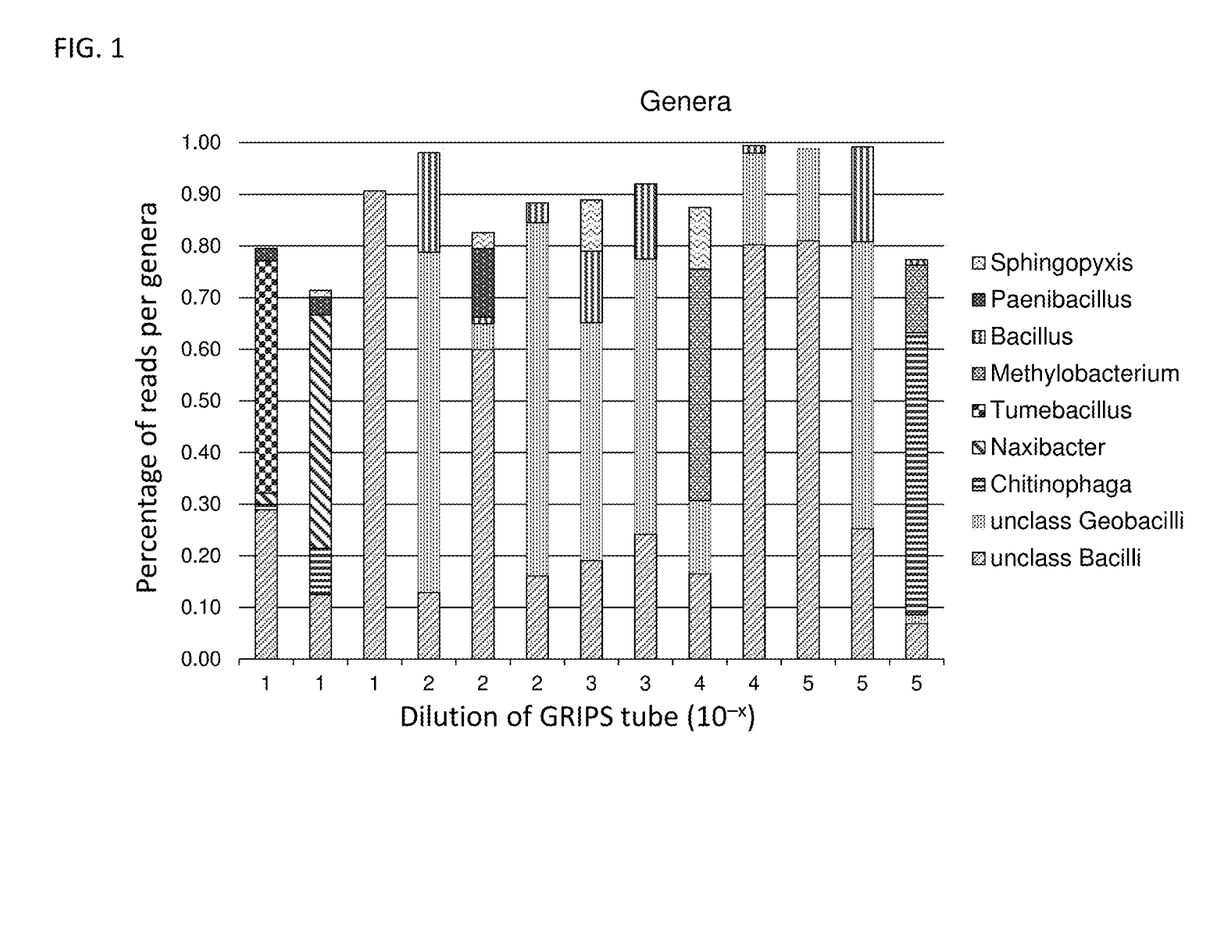
FIG. 1 shows numerically dominant genera detected by targeted metagenomic analysis of PCR-amplified 16S rRNA gene fragments. Values along the X-axis represent the dilution (10-x) of each GRIPS tube. Values along the Y-axis represent the percentage of reads classified in the indicated genera. For clarity, only genera that accounted for greater than 10% of the reads generated from a particular tube are shown.

The GRIPS described above reduced the bacterial diversity of the root microbiome dramatically, as assessed by next generation sequencing of PCR-amplified 16 rRNA gene fragments. This metagenomic analysis also revealed systems enriched with previously uncultured bacteria, including *Tumebacillus* species and unclassified *Bacillus* species (FIG. 1).

Figure 2:
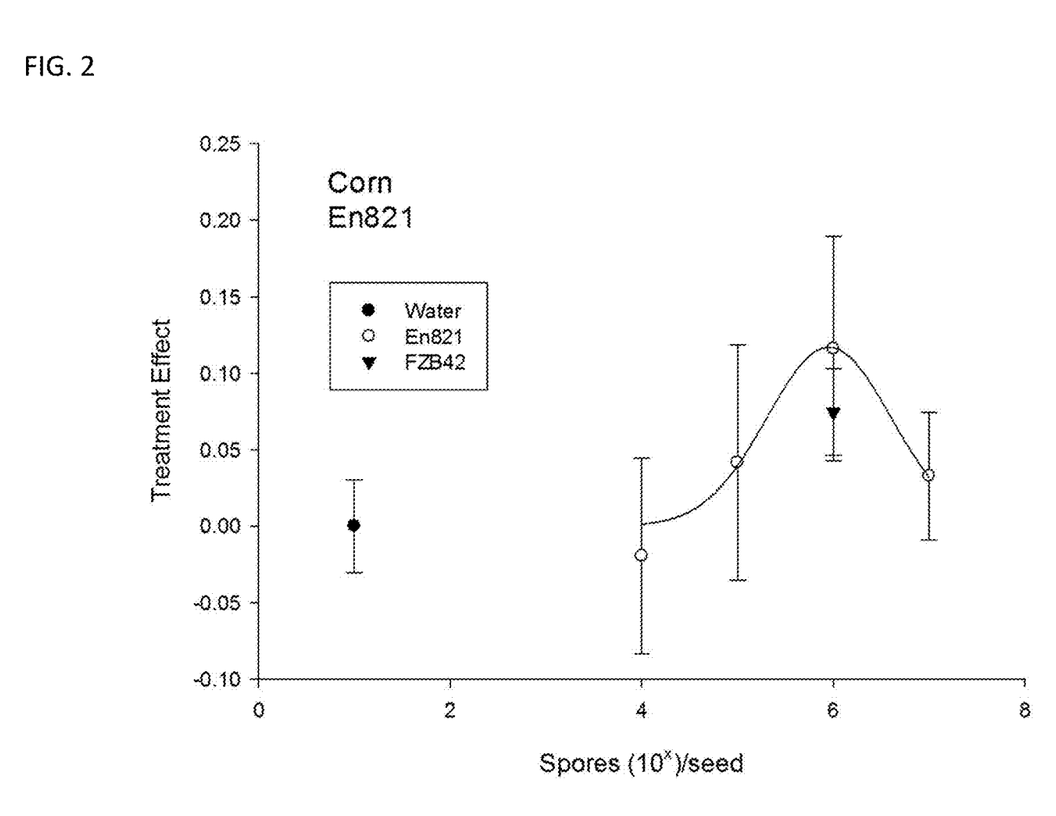
FIG. 2 shows plant growth response to isolate En.821. Corn was grown in a glasshouse in field soil. Seeds received the indicated dilution of overnight cultures of spores prepared from En821 Spores generated from the positive control (*B. amyloliquefaciens* FZB42) were diluted to $10^{-6}$. Treatment response represents the mean of biomass (shoot, root, and height) of treatments divided by the corresponding values for water controls. Bars represent standard error. The application of En821 significantly increased growth, as assessed by MANOVA of biomass parameters (Wilks' Lambda=0.013).
Figure 3:
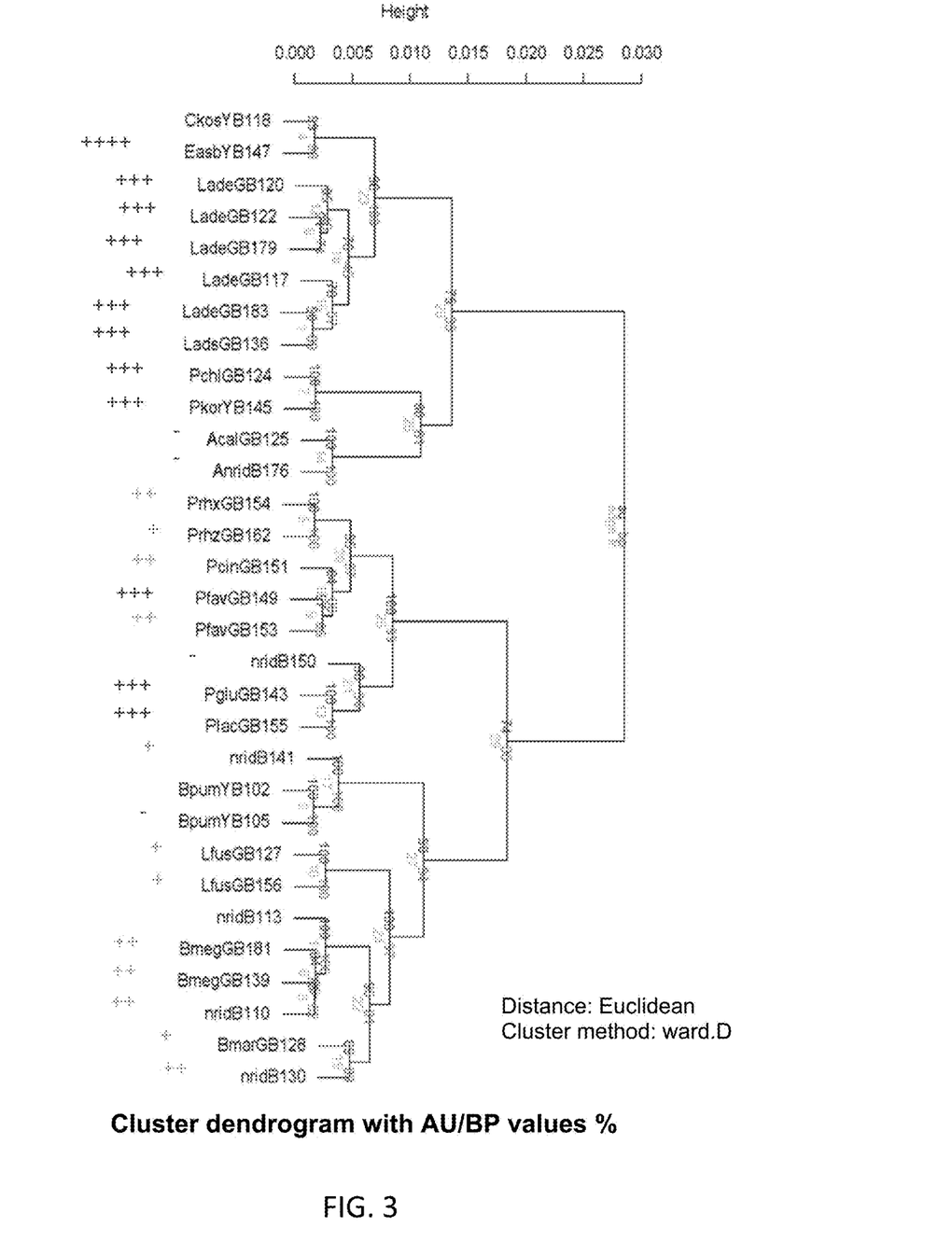
FIG. 3 shows a phylogenetic tree calculated from protein spectra generated by MALDI-TOF. The first four letters of each isolate indicates their species: Bmar (*Bacillus marinus*), etc. Red and green numbers indicate confidence of branching order as assessed by bootstrap analysis, which were calculated in Pvclust [157]. Positive signs indicate IAA production from strong (red), to moderate (yellow), to weak (green) or not detectable (–). IAA was measured colormetrically with Salkowski's reagent as described previously [111].

Using this system, over 500 bacteria were isolated, as well as over 300 from the source soil. Several hundred of these isolates were classified based on protein spectra generated by MALDI-TOF mass spectrometry (7, 26). This library contained several bacteria that show promise as plant growth-promoting inoculants for agriculture. One of these isolates, En821, outperformed the commercially available strain (FZB42) of *B. amyloliquefaciens* subsp. *plantarum* in terms of promotion of corn and soybean seedling growth (FIG. 2).

Example 2. GRIPS

The basic approach entails application of a gnotobiotic system, where plants establish a microbial community of limited diversity, relative to the source community. This entails inoculating surface-sterilized seeds with dilutions generated from soil slurries. The seeds are planted in a Gnotobiotic Rhizobacteria Isolation Plant System (GRIPS). The GRIPS builds on the concepts presented by Simons et al. [27], where seedlings are grown in axenic conditions in glass tubes to study plant-microbe interactions.

To prove the concept of this approach, libraries of aerobic, spore-forming, heterotrophs were generated using GRIPS and, in parallel, from the source soil. A heat-treated inoculum generated from soil was used to enrich for spore-forming PGPR. This inoculum was serially diluted and used to treat surface-sterilized wheat seeds that were planted in GRIPS. Briefly, large glass test tubes were filled to half their volume with air-dried soil/sand (50/50) mixtures and covered with a cotton plug and autoclaved. After sterilization, the rhizoplane-inoculated wheat seeds were planted and sterile water was added to 60% of the water holding capacity of the soil/sand mix. Control systems were generated as above in fresh, not autoclaved, soil.

Tubes were incubated for two weeks, and then, following harvest, a rhizoplane slurry was generated for microbial community analysis and isolation. Microbial community analysis was conducted by sequencing using Ion Torrent platform of 16S rRNA gene fragments generated by PCR. Libraries of isolates were generated by first heat-treating to select for spore-formers then plating serial dilutions on dilute Tryptic Soy Agar, which supports a broad range of readily culturable bacteria. The system dramatically reduced the bacterial diversity of the root microbiome to a tractable level, as assessed by metagenomics. The metagenome of the bulk soil contained 381 to 425 genera. The metagenome of the GRIPS samples contained 12 to 96 genera. This metagenomic analysis also revealed systems enriched with previously uncultured bacteria, including *Tumebacillus*. Importantly, GRIPS produced tubes with different communities, which effectively segregates the root microbiome into distinct and tractable communities. The reduced complexity of these communities will facilitate metagenomic analysis and assembly of individual genomes in particular. As discussed below, this metagenomic analysis informs the isolation strategy.

The abundance of *Chitinophaga* species, and other non-spore forming genera in some GRIPS samples, suggests that the system is not perfectly axenic; however, generally the system supported communities enriched in species associated with spore formation. Importantly, GRIPS produced tubes with different communities, which effectively segregates the root microbiome into distinct and tractable communities. The reduced complexity of these communities will facilitate metagenomic analysis and assembly of individual genomes.

Using this system, >500 rhizobacteria were isolated and, in parallel, a control library of >300 rhizobacteria from the source soil. Several hundred of these isolates were classified based on protein spectra generated by MALDI-TOF and two prospects were identified for greenhouse trials. A prospect, En120, was identified in the control library based on the similarity to the reference spectra for *B. amyloliquefaciens*. En120 promoted corn and soybean seedling growth in greenhouse trials at least as well as the well-documented PGPR strain FZB42. FZB42, and the closely related strain GB03, are commercially available plant growth promoting subspecies of *B. amyloliquefaciens* [86]. A prospect, En821, was identified in a GRIPS library based on similarity to the reference spectra for *B. mojavensis*. En821 also promoted corn (FIG. 2) and soybean growth in greenhouse trials. The library of isolates generated from the GRIPS showed less diversity in terms of protein spectra than the control library, but as the metagenomic analysis revealed, the GRIPS contained a different set of microbes than would be obtained with conventional techniques. This confirms the system isolates novel microbes with PGPR potential.

Example 3. Developing Field-Tested PGPR i) Determine if the high throughput *B. distachyon* phenotyping system identifies PGPR that promote crop yield in the field.

ii) Determine correspondence between clusters of rhizobacteria, as defined by protein spectra, and promotion of the growth of *B. distachyon*.

iii) Apply GRIPS to recover a second generation of PGPR.

Example 4. Selection of Prospects for Field Trials

MALDI-TOF will be applied to dereplicate libraries of isolates prior to screening these isolates for plant growth promotion in bioassays. This assumes that MALDItypes within a cluster are similar to each other, in terms of this trait. MALDI-TOF identification generally agrees with microbiology phenotyping methods [78], and traits associated with PGPR; it is proposed that clusters of MALDItypes correspond to plant growth promotion in the field. This will be tested with isolates from the library. The genomes of multiple representatives of each MALDItype will be sequenced to provide a polyphasic microbial identification [103]. Ten isolates will be selected for field trials depending on their novelty, genes associated with plant growth promotion, such as genes that code for ACC deaminase [129], and, by analysis of their genomes with antiSMASH 2.0, biosynthetic pathways of potential value [84]. Biosafety Level II precautions will be taken with all isolates. PGPR should be treated as a biosafety hazard and tested for pathogenicity [162]. Heat-treatment is included in the isolation protocol, and many *Bacillus* species, including PGPR, readily isolated from soils are human pathogens [105]. MALDI-TOF and sequencing will be used to identify pathogens. Commercially available databases of protein mass spectra generated from bacteria MALDI-TOF allow the rapid identification of bacteria and previously described pathogens [78]; however, a previously undescribed pathogen could be isolated. To detect, these pathogens, draft genomes of microbes that do not show similarity will be assembled, in terms of protein spectra, to well-characterized bacteria in the MALDI-TOF. Contigs from these genomes will be searched for pathogenicity islands, and virulence genes, by using the pathogenicity island database [59].

Example 5. GRIPS

Figure 4:
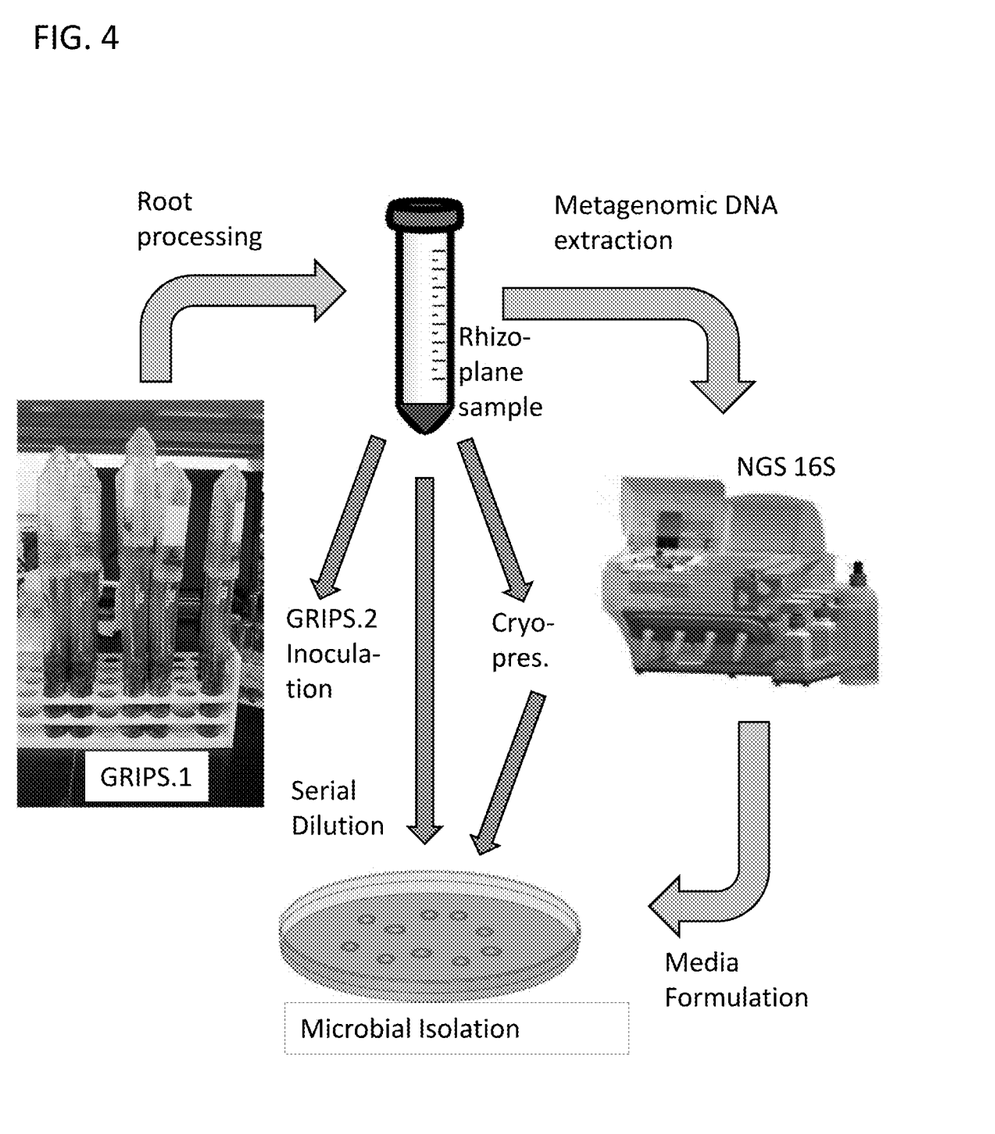
FIG. 4 shows a schematic of GRIPS workflow. The process starts by inoculating surface-sterilized wheat seed and sowing GRIPS. 1. At harvest roots are processed to generate a rhizoplane sample, which is used to inoculated GRIPS. 2, serially diluted for plating and subsequent microbial isolation and, in parallel, cryopreserved and analyzed by next-generation sequencing (NGS) of PCR-amplified 16S rRNA genes. Sequence analysis informs media formulation.

Soil used in the preliminary work described above will be resampled to establish GRIPS.1. This soil has already yielded promising leads that promote plant growth and its potential is far from exhausted. Slurries generated from GRIPS.1 will be used to inoculate GRIPS.2 as illustrated in FIG. 4. GRIPS.1 will be established in sets of 48 tubes to generate an array of plants. This will allow for six-fold replication of four treatments and two controls. GRIPS.1 will be inoculated with heated and non-heated treatments. The heated treatments will be diluted 10-1 and 10-2. The non-heated treatments will be inoculated with 10-3 and 10-4 dilutions. At harvest, plant growth and root phenotype data will be collected and rhizoplane samples will be generated for metagenomic analyses, microbial isolation and inoculation of GRIPS.2. Plant growth data will allow identification of systems with larger plants, and presumably a population of beneficial microbes to prioritize the isolation strategy.

Example 6. Metagenomic Analysis to Assess Diversity and Inform Media Formulation Targeted metagenomic analysis of rhizoplane samples generated in GRIPS.1 will be used to prioritize samples with potentially valuable rhizobacteria and inform media formulation. Semi-conductor sequencing of PCR 16S rRNA gene amplicons will be applied as described previously [17, 163], to identify the dominant rhizobacteria in each system. This will confirm that the GRIPS.1 reduced the diversity of the rhizoplane to tractable levels and, in the case of systems inoculated with heated slurries, selected for aerobic, spore formers. Ribosomal sequences will be used, and the media formulation databases KOMODO [21, 37] and MediaDB [24], to select media formulations optimized for the nutritional needs of targeted ribotypes. Media components will be autoclaved separately from each other, to avoid creation of toxic by-products [30] and solidify the media with gelling agents, as semi-solid media recovers more representative bacteria from soil than liquid media [153]. Multiple gelling agents, will be tried, including Gellan gum [10, 20], to improve microbial recovery [6].

Example 7. Field Trials

GRIPS will generate an array of seedlings where the diversity of the plant microbiome is dispersed into dozens of gnotobiotic tubes. Each of these systems will model plant-microbe interactions and facilitate identification of microbial communities, and even particular microbes, which correspond to larger seedlings. Each of these systems will capture a subset of the dominant members of the plant microbiome and, by targeted metagenomic analysis of rhizoplane samples, systems can be identified that contain rhizobacteria of potential value and formulate media to recover these PGPR. By using rhizoplane samples from GRIPS.1 to inoculate GRIPS.2 the microbiomes will be further simplified in these systems and lead to systems with tractable rhizobacterial diversity. The simplified plant microbiome in GRIPS should also facilitate de novo assembly of the genomes of yet-to-be cultured rhizobacteria.

All publications, patents, and patent applications mentioned in this specification are incorporated herein by reference to the same extent as if each independent publication or patent application was specifically and individually indicated to be incorporated by reference.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

1. Abbasi, M. K. (2015) Isolation and characterization of plant growth-promoting rhizobacteria from wheat rhizosphere and their effect on plant growth promotion. *Frontiers in Microbiology* 6, 198.
2. Barbosa, T. M., Serra, C. R., La Ragione, R. M., et al. (2005) Screening for *Bacillus* Isolates in the Broiler Gastrointestinal Tract. *Appl Environl Microbiol* 71, 968-978.
3. Belimov, A. A., Safronova, V. I., Sergeyeva, T. A., et al. (2001) Characterization of plant growth promoting rhizobacteria isolated from polluted soils and containing 1-aminocyclopropane-1-carboxylate deaminase. *C J Microbiol* 47, 642-652.
4. Brader, G., Compant, S., Mitter, B., et al. (2014) Metabolic potential of endophytic bacteria. *Cur Op Biotech* 27, 30-37.
5. Brígido, C. and Glick, B. (2015) Phytoremediation using rhizobia. In *Phytoremediation* (Ansari, A. A., et al., eds), pp. 95-114, Springer International Publishing.
6. Das, N., Triparthi, N., Basu, S., et al. (2015) Progress in the development of gelling agents for improved culturability of microorganisms. *Front Microbiol* 6, 698.
7. Ghyselinck, J., Van Hoorde, K., Hoste, B., et al. (2011) Evaluation of MALDI-TOF MS as a tool for high-throughput dereplication. *J Microbiol Methods* 86, 327-336.
8. Gordon, J. I., Faith, J. J., McNulty, N. P., et al. (2014) Cultured collection of gut microbial community. US20140045744.
9. Guenet, B., Leloup, J., Hartmann, C., et al. (2011) A new protocol for an artificial soil to analyse soil microbiological processes. *Applied Soil Ecology* 48, 243-246.
10. Janssen, P. H., Yates, P. S., Grinton, B. E., et al. (2002) Improved culturability of soil bacteria and isolation in pure culture of novel members of the divisions *Acidobacteria, Actinobacteria, Proteobacteria*, and *Verrucomicrobia*. *Appl Environl Microbiol* 68, 2391-2396.
11. Jung, D., Seo, E.-Y., Epstein, S. S., et al. (2014) Application of a new cultivation technology, I-tip, for studying microbial diversity in freshwater sponges of Lake Baikal, Russia. *FEMS Microbiology Ecology* 90, 417-423.
12. Kaeberlein, T., Lewis, K., and Epstein, S. S. (2002) Isolating "uncultivable" microorganisms in pure culture in a simulated natural environment. *Science* 296, 1127-1129.
13. Kennedy, J., Marchesi, J., and Dobson, A. W. (2007) Metagenomic approaches to exploit the biotechnological potential of the microbial consortia of marine sponges. *Appl Microbiol Biotechnol* 75, 11-20.
14. Kumar, P., Dubey, R. C., and Maheshwari, D. K. (2012) *Bacillus* strains isolated from rhizosphere showed plant growth promoting and antagonistic activity against phytopathogens. *Microbiol Res* 167, 493-499.
15. Labbé, J. L., Weston, D. J., Dunkirk, N., et al. (2014) Newly identified helper bacteria stimulate ectomycorrhizal formation in Populus. *Front Plant Sci* 5. 579
16. Lagier, J.-C., Hugon, P., Khelaifia, S., et al. (2015) The rebirth of culture in microbiology through the example of culturomics to study human gut microbiota. *Clinical Microbiology Reviews* 28, 237-264.
17. Menchaca, A. C., Visi, D. K., Strey, O. F., et al. (2013) Preliminary assessment of microbiome changes following blood-feeding and survivorship in the *Amblyomma americanum* nymph-to-adult transition using semiconductor sequencing. *PLoS ONE* 8, e67129.
18. Newman, D. J. and Cragg, G. M. (2015) Endophytic and epiphytic microbes as "sources" of bioactive agents. *Front Chem* 3, 34.
19. Nunes da Rocha, U., van Overbeek, L., and van Elsas, J. D. (2009) Exploration of hitherto-uncultured bacteria from the rhizosphere. *FEMS Microbiol Ecol* 69, 313-328.
20. Nyonyo, T., Shinkai, T., and Mitsumori, M. (2014) Improved culturability of cellulolytic rumen bacteria and phylogenetic diversity of culturable cellulolytic and xylanolytic bacteria newly isolated from the bovine rumen. *FEMS Microbiol Ecol* 88, 528-537.
21. Oberhardt, M. A., Zarecki, R., Gronow, S., et al. (2015) Harnessing the landscape of microbial culture media to predict new organism-media pairings. *Nat Commun* 6, 8493.
22. Raaijmakers, J. M. and Mazzola, M. (2012) Diversity and natural functions of antibiotics produced by beneficial and plant pathogenic bacteria. *Ann Rev Phytopathol* 50, 403-424.
23. Rettedal, E. A., Gumpert, H., and Sommer, M. O. A. (2014) Cultivation-based multiplex phenotyping of human gut microbiota allows targeted recovery of previously uncultured bacteria. *Nat Commun* 5, 4714.
24. Richards, M. A., Cassen, V., Heavner, B. D., et al. (2014) MediaDB: A database of microbial growth conditions in defined media. *PLoS ONE* 9, e103548.
25. Ruff, W. E., Vieira, S. M., and Kriegel, M. A. (2015) The Role of the Gut Microbiota in the Pathogenesis of Antiphospholipid Syndrome. *Cur Rheum Rep* 17, 472-472.
26. Sauer, S., Freiwald, A., Maier, T., et al. (2008) Classification and identification of bacteria by mass spectrometry and computational analysis. *PLoS One* 3, e2843.
27. Simons, M., van der Bij, A. J., Brand, I., et al. (1996) Gnotobiotic system for studying rhizosphere colonization by plant growth-promoting *Pseudomonas* bacteria. *Mol Plant-Microbe Inter: MPMI* 9, 600-607.
28. Song, W., Pijanowski, B. C., and Tayyebi, A. (2015) Urban expansion and its consumption of high-quality farmland in Beijing, China. *Ecol Ind* 54, 60-70.
29. Stewart, E. J. (2012) Growing unculturable bacteria. *J Bacteriol* 194, 4151-4160.

30. Tanaka, T., Kawasaki, K., Daimon, S., et al. (2014) A hidden pitfall in agar media preparation undermines cultivability of microorganisms. *Appl Environ Microbiol* 80, 7659-7666.
31. Tkacz, A. and Poole, P. (2015) Role of root microbiota in plant productivity. *J Exper Bot* 66, 2167-2175.
32. Trevors, J. T. (1996) Sterilization and inhibition of microbial activity in soil. *J Microbiol Meth* 26, 53-59.
33. Ugoji, E., Laing, M., and Hunter, C. (2005) Colonization of *Bacillus* spp. on seeds and in plant rhizoplane. *J Environ Biol* 26, 459-466.
34. Wiese, J., Thiel, V., Nagel, K., et al. (2009) Diversity of antibiotic-active bacteria associated with the brown alga *Laminaria saccharina* from the Baltic Sea. *Mar Biotechnol* 11, 287-300.
35. Wilson, M. C., Mori, T., Ruckert, C., et al. (2014) An environmental bacterial taxon with a large and distinct metabolic repertoire. *Nature* 506, 58-62.
36. Yan, L., Boyd, K. G., Adams, D. R., et al. (2003) Biofilm-specific cross-species induction of antimicrobial compounds in Bacilli. *Appl Environ Microbiol* 69, 3719-3727.
37. Zarecki, R., Oberhardt, M. A., Reshef, L., et al. (2014) A novel nutritional predictor links microbial fastidiousness with lowered ubiquity, growth rate, and cooperativeness. *PLoS Comput Biol* 10, e1003726.
38. WILLIAMS, S. T. and DAVIES, F. L. (1965) Use of Antibiotics for Selective Isolation and Enumeration of Actinomycetes in Soil. Microbiology 38, 251-261.
39. Schrey, S. D., Erkenbrack, E., Frith, E., et al. (2012) Production of fungal and bacterial growth modulating secondary metabolites is widespread among mycorrhiza-associated streptomycetes. BMC Microbiology 12, 164-164.
40. Liu, Y., Lai, Q., Dong, C., et al. (2013) Phylogenetic Diversity of the <italic>Bacillus pumilus</italic> Group and the Marine Ecotype Revealed by Multilocus Sequence Analysis. PLoS ONE 8, e80097.
41. Pérez-Yépez, J., Armas-Capote, N., Velázquez, E., et al. (2014) Evaluation of seven housekeeping genes for multilocus sequence analysis of the genus *Mesorhizobium*: Resolving the taxonomic affiliation of the *Cicer canariense* rhizobia. Systematic and Applied Microbiology 37, 553-559.
42. Chernin, I., Ismailov, Z., Haran, S., et al. (1995) Chitinolytic *Enterobacter agglomerans* antagonistic to fungal plant pathogens. Appl Environ Microbiol 61.
43. Penrose, D. and Glick, B. (2003) Methods for isolating and characterizing ACC deaminase-containing plant growth-promoting rhizobacteria. Physiol Plantarum 118, 10-15.
44. Ray D K, Mueller N D, West P C, Foley J A. Yield trends are insufficient to double global crop production by 2050. PLoS ONE. 2013; 8(6):e66428. doi: 10.1371/journal.pone.0066428.
45. Bresson J, Vasseur F, Dauzat M, Labadie M, Varoquaux F, Touraine B, et al. Interact to survive: *Phyllobacterium brassicacearum* improves *Arabidopsis* tolerance to severe water deficit and growth recovery. PLoS ONE. 2014; 9(9):e107607. doi: 10.1371/journal.pone.0107607.
46. Chowdhury S P, Dietel K, Rändler M, Schmid M, Junge H, Borriss R, et al. Effects of *Bacillus amyloliquefaciens* FZB42 on lettuce growth and health under pathogen pressure and its impact on the rhizosphere bacterial community. PLoS ONE. 2013; 8(7):e68818. doi: 10.1371/journal.pone.0068818.
47. Unpublished Source. Biofertilizers market analysis by product (nitrogen fixing, phosphate solubilizing), by application (seed treatment, soil Treatment) and segment forecasts to 2022. Available from: http://www.grandviewresearch.com/industry-analysis/biofertilizers-industry.
48. Culligan E P, Sleator R D, Marchesi J R, Hill C. Metagenomics and novel gene discovery. Virulence. 2014; 5(3):399-412. doi: 10.4161/viru.27208.
49. Charlop-Powers Z, Milshteyn A, Brady S F. Metagenomic small molecule discovery methods. Current Opinion in Microbiology. 2014; 19:70-5. doi:.
50. Roy M, Srivastava R. Assembling BNF system in rice plant: frontier areas of research. Curr Sci. 2013; 104:3-10.
51. Howe A C, Jansson J K, Malfatti S A, Tringe S G, Tiedje J M, Brown C T. Tackling soil diversity with the assembly of large, complex metagenomes. PNAS. 2014; 111(13): 4904-9. doi: 10.1073/pnas.1402564111.
52. Nielsen H B, Almeida M, Juncker A S, Rasmussen S, Li J, Sunagawa S, et al. Identification and assembly of genomes and genetic elements in complex metagenomic samples without using reference genomes. Nat Biotech. 2014; 32(8):822-8. doi: 10.1038/nbt.2939.
53. Sharon I, Kertesz M, Hug L A, Pushkarev D, Blauwkamp T A, Castelle C J, et al. Accurate, multi-kb reads resolve complex populations and detect rare microorganisms. Genome Research. 2015; 25(4):534-43. doi: 10.1101/gr.183012.114.
54. Blainey P C. The future is now: single-cell genomics of bacteria and archaea. FEMS Microbiology Reviews. 2013; 37(3):407-27. doi: 10.1111/1574-6976.12015.
55. Gawad C, Koh W, Quake S R. Single-cell genome sequencing: current state of the science. Nat Rev Genet. 2016; 17(3):175-88. doi: 10.1038/nrg.2015.16.
56. Delmont T O, Eren A M, Maccario L, Prestat E, Esen Ö C, Pelletier E, et al. Reconstructing rare soil microbial genomes using in situ enrichments and metagenomics. Frontiers in Microbiology. 2015; 6(358). doi: 10.3389/fmicb.2015.00358.
57. LaMontagne M G, Schimel J P, Holden P A. Comparison of subsurface and surface soil bacterial communities in california grassland as assessed by terminal restriction fragment length polymorphisms of PCR-amplified 16S rRNA genes. Microbial Ecology. 2003; 46(2):216-27. doi: 10.1007/s00248-003-1006-y.
58. Choi J, Yang F, Stepanauskas R, Cardenas E, Garoutte A, Williams R, et al. RefSoil: A reference database of soil microbial genomes. bioRxiv. 2016. doi: 10.1101/053397.
59. Yoon S H, Park Y-K, Kim J F. PAIDB v2.0: exploration and analysis of pathogenicity and resistance islands. Nucleic Acids Research. 2015; 43(D1):D624-D30. doi: 10.1093/nar/gku985.
60. Sanders E R, Hirsch A M. Immersing undergraduate students into research on the metagenomics of the plant rhizosphere: a pedagogical strategy to engage civic-mindedness and retain undergraduates in STEM. Frontiers in Plant Science. 2014; 5(157). doi: 10.3389/fpls.2014.00157.
61. Zaaijer S, Erlich Y. Using mobile sequencers in an academic classroom. eLife. 2016; 5:e14258. doi: 10.7554/eLife.14258.
62. Dang J, Mendez P, Lee S, Kim J W, Yoon J H, Kim T W, et al. Development of a robust DNA quality and quantity assessment qPCR assay for targeted next-generation sequencing library preparation. International Journal of Oncology. 2016. Epub 2016/08/12. doi: 10.3892/ijo.2016.3654. PubMed PMID: 27511764.

63. Jovel J, Patterson J, Wang W, Hotte N, O'Keefe S, Mitchel T, et al. Characterization of the gut microbiome using 16S or shotgun metagenomics. Frontiers in Microbiology. 2016; 7(459). doi: 10.3389/fmicb.2016.00459.
64. Lugli G A, Milani C, Mancabelli L, van Sinderen D, Ventura M. MEGAnnotator: a user-friendly pipeline for microbial genomes assembly and annotation. FEMS Microbiology Letters. 2016; 363(7). doi: 10.1093/femsle/fnw049.
65. Urban J M, Bliss J, Lawrence C E, Gerbi S A. Sequencing ultra-long DNA molecules with the Oxford Nanopore MinION. bioRxiv. 2015. doi: 10.1101/019281.
66. Watson M, Thomson M, Risse J, Talbot R, Santoyo-Lopez J, Gharbi K, et al. poRe: an R package for the visualization and analysis of nanopore sequencing data. Bioinformatics. 2015; 31(1):114-5. doi: 10.1093/bioinformatics/btu590.
67. Cao M D, Nguyen S H, Ganesamoorthy D, Elliott A G, Cooper M A, Coin L J M. Scaffolding and completing genome assemblies in real-time with nanopore sequencing. Nature Communications. 2017; 8:14515. doi: 10.1038/ncomms14515.
68. Mikheenko A, Saveliev V, Gurevich A. MetaQUAST: evaluation of metagenome assemblies. Bioinformatics. 2016; 32(7):1088-90. doi: 10.1093/bioinformatics/btv697.
69. Adesemoye A, Kloepper J. (2009) Plant-microbes interactions in enhanced fertilizer-use efficiency. Applied Microbiology and Biotechnology 85:1-12.
70. Ahmad F, Ahmad I, Khan M S. (2008) Screening of free-living rhizospheric bacteria for their multiple plant growth promoting activities. Microbiological Research 163:173-181.
71. Ahmad F, Babalola O, Tak H. (2012) Potential of MALDI-TOF mass spectrometry as a rapid detection technique in plant pathology: identification of plant-associated microorganisms. Analytical and Bioanalytical Chemistry 404:1247-1255.
72. Akiyama H, Yan X, Yagi K. (2010) Evaluation of effectiveness of enhanced-efficiency fertilizers as mitigation options for N2O and NO emissions from agricultural soils: meta-analysis. Global Change Biology 16:1837-1846.
73. Ali M B, McNear D H. (2014) Induced transcriptional profiling of phenylpropanoid pathway genes increased flavonoid and lignin content in *Arabidopsis* leaves in response to microbial products. BMC Plant Biology 14:84.
74. Alivisatos A P, Blaser M J, Brodie E L, Chun M, Dangl J L, Donohue T J, et al. (2015) A unified initiative to harness Earth's microbiomes. Science 350:507-508.
75. Alves S C, Worland B, Thole V, Snape J W, Bevan M W, Vain P. (2009) A protocol for *Agrobacterium*-mediated transformation of *Brachypodium distachyon* community standard line Bd21. Nature Protocols 4:638-649.
76. Ambrosini A, Beneduzi A, Stefanski T, Pinheiro F, Vargas L, Passaglia L. (2012) Screening of plant growth promoting rhizobacteria isolated from sunflower *Helianthus annuus* L. Plant & Soil 356:245-264.
77. Baig K, Arshad M, Shaharoona B, Khalid A, Ahmed I. (2012) Comparative effectiveness of *Bacillus* spp. possessing either dual or single growth-promoting traits for improving phosphorus uptake, growth and yield of wheat (*Triticum aestivum* L.). Annals of Microbiology 62:1109-1119.
78. Barberis C, Almuzara M, Join-Lambert O, Ramírez M S, Famiglietti A, Vay C. (2014) Comparison of the Bruker MALDI-TOF mass spectrometry system and conventional phenotypic methods for identification of Gram-positive rods. PLoS ONE 9:e106303.
79. Barnawal D, Maji D, Bharti N, Chanotiya C, Kalra A. (2013) ACC deaminase-containing *Bacillus subtilis* reduces stress ethylene-induced damage and improves mycorrhizal colonization and rhizobial nodulation in *Trigonella foenum-graecum* under drought stress. Journal of Plant Growth Regulation 32:809-822.
80. Bashan Y, Kamnev A, De-Bashan L. (2013) Tricalcium phosphate is inappropriate as a universal selection factor for isolating and testing phosphate-solubilizing bacteria that enhance plant growth: a proposal for an alternative procedure. Biological Fertility of Soils 49:465-479.
81. Baym M, Kryazhimskiy S, Lieberman T D, Chung H, Desai M M, Kishony R. (2015) Inexpensive Multiplexed Library Preparation for Megabase-Sized Genomes. PLoS ONE 10:e0128036.
82. Berendsen R L, Pieterse C M J, Bakker P A H M. (2012) The rhizosphere microbiome and plant health. Trends in Plant Science 17:478-486.
83. Berg G. (2009) Plant-microbe interactions promoting plant growth and health: perspectives for controlled use of microorganisms in agriculture. Applied Microbiology and Biotechnology 84:11-18.
84. Blin K, Medema M H, Kazempour D, Fischbach M A, Breitling R, Takano E, et al. (2013) antiSMASH 2.0—a versatile platform for genome mining of secondary metabolite producers. Nucleic Acids Research 41:W204-W212.
85. Bomgardner M M. (2013) Microbes power crop alliance. Chemical & Engineering News 91:6.
86. Borriss R. Use of plant-associated *Bacillus* strains as biofertilizers and biocontrol agents in agriculture. In: Maheshwari D K, editor. Bacteria in Agrobiology: Plant Growth Responses: Springer Berlin Heidelberg; 2011. p. 41-76.
87. Bragg J N, Wu J, Gordon S P, Guttman M E, Thilmony R, Lazo G R, et al. (2012) Generation and characterization of the Western Regional Research Center *Brachypodium* T-DNA insertional mutant collection. PLoS ONE 7:e41916.
88. Brkljacic J, Grotewold E, Scholl R, Mockler T, Garvin D F, Vain P, et al. (2011) *Brachypodium* as a model for the grasses: today and the future. Plant Physiology 157:3-13.
89. Calvo P, Watts D B, Ames R N, Kloepper J W, Torbert H A. (2013) Microbial-Based Inoculants Impact Nitrous Oxide Emissions from an Incubated Soil Medium Containing Urea Fertilizers. Journal of Environmental Quality 42:704-712.
90. Cardinale M, Ratering S, Suarez C, Zapata Montoya A M, Geissler-Plaum R, Schnell S. (2015) Paradox of plant growth promotion potential of rhizobacteria and their actual promotion effect on growth of barley (*Hordeum vulgare* L.) under salt stress. Microbiological Research 181:22-32.
91. Cawoy Hln, Bettiol W, Fickers P, Ongena M. *Bacillus*-based biological control of plant diseases. In: Stoytcheva M, editor. Pesticides in the Modern World—Pesticides Use and Management 2011.
92. Choo J M, Leong L E X, Rogers G B. (2015) Sample storage conditions significantly influence faecal microbiome profiles. Scientific Reports 5:16350.
93. Cui H, Wang C, Gu Z, Zhu H, Fu S, Yao Q. (2014) Evaluation of soil storage methods for soil microbial community using genetic and metabolic fingerprintings. European Journal of Soil Biology 63:55-63.

94. Dai A. (2011) Drought under global warming: a review. Wiley Interdisciplinary Reviews: Climate Change 2:45-65.
95. Dalmais M, Antelme S, Ho-Yue-Kuang S, Wang Y, Darracq O, d?Yvoire M B, et al. (2013) A TILLING platform for functional genomics in *Brachypodium distachyon*. PLoS ONE 8:e65503.
96. Delgado-Baquerizo M, Maestre F T, Reich P B, Jeffries T C, Gaitan J J, Encinar D, et al. (2016) Microbial diversity drives multifunctionality in terrestrial ecosystems. Nat Commun 7:e10541.
97. Delmont T O, Eren A M, Maccario L, Prestat E, Esen Ö C, Pelletier E, et al. (2015) Reconstructing rare soil microbial genomes using in situ enrichments and metagenomics. Frontiers in Microbiology 6:e358.
98. do Amaral F P, Pankievicz V C S, Arisi A C M, de Souza E M, Pedrosa F, Stacey G. (2016) Differential growth responses of *Brachypodium distachyon* genotypes to inoculation with plant growth promoting rhizobacteria. Plant Molecular Biology 90:689-697.
99. Draper J, Mur L A J, Jenkins G, Ghosh-Biswas G C, Bablak P, Hasterok R, et al. (2001) *Brachypodium distachyon*. a new model system for functional genomics in grasses. Plant Physiology 127:1539-1555.
100. Fahlgren N, Gehan M A, Baxter I. (2015) Lights, camera, action: high-throughput plant phenotyping is ready for a close-up. Current Opinion in Plant Biology 24:93-99.
101. Figueiredo M, Seldin L, de Araujo F, Mariano R. Plant growth promoting rhizobacteria: fundamentals and applications. In: Maheshwari D K, editor. Plant Growth and Health Promoting Bacteria. Microbiology Monographs. 18: Springer Berlin Heidelberg; 2011. p. 21-43.
102. Fitzgerald T L, Powell J J, Schneebeli K, Hsia M M, Gardiner D M, Bragg J N, et al. (2015) *Brachypodium* as an emerging model for cereal-pathogen interactions. Annals of Botany 115:717-731.
103. Fournier P-E, Lagier J-C, Dubourg G, Raoult D. (2015) From culturomics to taxonomogenomics: A need to change the taxonomy of prokaryotes in clinical microbiology. Anaerobe 36:73-78.
104. Gagné-Bourque F, Mayer B F, Charron J-B, Vali H, Bertrand A, Jabaji S. (2015) Accelerated growth rate and increased drought stress resilience of the model grass *Brachypodium distachyon* colonized by *Bacillus subtilis* B26. PLoS ONE 10:e0130456.
105. Ganz H H, Turner W C, Brodie E L, Kusters M, Shi Y, Sibanda H, et al. (2014) Interactions between *Bacillus anthracis* and plants may promote anthrax transmission. PLoS Negl Trop Dis 8:e2903.
106. Garrity G M. (2016) A New Genomics-Driven Taxonomy of Bacteria and Archaea: Are We There Yet? Journal of Clinical Microbiology 54:1956-1963.
107. Gibb S, Strimmer K. (2012) MALDIquant: a versatile R package for the analysis of mass spectrometry data. Bioinformatics 28:2270-2271.
108. Gillam C. 2015 DuPont buying microbiome firm, seeks edge in emerging crop products. Reutershttp://www.reuters.com/article/2015/04/22/us-dupont-acquisition-idUSKBN0ND22G20150422#JYswpDProbU2EZtD.99.
109. Girin T, David L C, Chardin C, Sibout R, Krapp A, Ferrario-Méry S, et al. (2014) *Brachypodium*: a promising hub between model species and cereals. Journal of Experimental Botany 65:5683-5696.
110. Glick B. (2014) Bacteria with ACC deaminase can promote plant growth and help to feed the world. Microbiol Res 169:30-39.
111. Glickmann E, Dessaux Y. (1995) A critical examination of the specificity of the Salkowski Reagent for indolic compounds produced by phytopathogenic bacteria. Applied and Environmental Microbiology 61:793-796.
112. Gordon J I, Faith J J, McNulty N P, Rey F E, Goodman A, Kallstrom G, et al., et al. (2012) Cultured collection of gut microbial community. Patent WO2012122522.
113. Gordon S P, Priest H, Des Marais D L, Schackwitz W, Figueroa M, Martin J, et al. (2014) Genome diversity in *Brachypodium distachyon*: deep sequencing of highly diverse inbred lines. The Plant Journal 79:361-374.
114. Granier C, Aguirrezabal L, Chenu K, Cookson S J, Dauzat M, Hamard P, et al. (2006) PHENOPSIS, an automated platform for reproducible phenotyping of plant responses to soil water deficit in *Arabidopsis thaliana* permitted the identification of an accession with low sensitivity to soil water deficit. New Phytologist 169:623-635.
115. Harman G E, Custis D B. (2015) Formulations of viable microorganisms and their methods of production and use. Patents. U.S. Pat. No. 9,090,884.
116. Harrison C. (2014) Patenting natural products just got harder. Nature Biotechnology 32:403-404.
117. Harvey A L, Edrada-Ebel R, Quinn R J. (2015) The re-emergence of natural products for drug discovery in the genomics era. Nature Review Drug Discovery 14:111-129.
118. Hoefman S, Van Hoorde K, Boon N, Vandamme P, De Vos P, Heylen K. (2012) Survival or revival: Long-term preservation induces a reversible viable but non-culturable state in methane-oxidizing bacteria. PLoS ONE 7:e34196.
119. Howard P. (2009) Visualizing consolidation in the global seed industry: 1996-2008. Sustainability 1:1266.
120. Initiative I B. (2010) Genome sequencing and analysis of the model grass *Brachypodium distachyon*. Nature 463:763-768.
121. Kellogg E A. (2015) *Brachypodium distachyon* as a Genetic Model System. Annual Review of Genetics 49:1-20.
122. Klappenbach J A, Dunbar J M, Schmidt T M. (2000) rRNA operon copy number reflects ecological strategies of bacteria. Applied and Environmental Microbiology 66:1328-1333.
123. Kothamasi D, Spurlock M, Kiers E T. (2011) Agricultural microbial resources: private property or global commons? Nature Biotechnology 29:1091-1093.
124. Kumar A, Kumar A, Pratush A. (2014) Molecular diversity and functional variability of environmental isolates of *Bacillus* species. SpringerPlus 3:312.
125. LaMontagne M G, Michel Jr F C, Holden P A, Reddy C A. (2002) Evaluation of extraction and purification methods for obtaining PCR-amplifiable DNA from compost for microbial community analysis. Journal of Microbiological Methods 49:255-264.
126. Lebeis S L. (2014) The potential for give and take in plant-microbiome relationships. Frontiers in Plant Science 5.
127. Leng P, Zhang Z, Pan G, Zhao M. (2011) Applications and development trends in biopesticides. African Journal of Biotechnology 10:19864-19873.
128. Leonetti J P, Texier S. (2015) Methods for isolating bacteria. Patent US20110294979.
129. Li Z, Chang S, Ye S, Chen M, Lin L, Li Y, et al. (2015) Differentiation of 1-aminocyclopropane-1-carboxylate (ACC) deaminase from its homologs is the key for identifying bacteria containing ACC deaminase. FEMS Microbiology Ecology 91:fv112.
130. Ling L L, Schneider T, Peoples A J, Spoering A L, Engels I, Conlon B P, et al. (2015) A new antibiotic kills pathogens without detectable resistance. Nature 517:455-459.
131. Luo Y, Cobb R E, Zhao H. (2014) Recent advances in natural product discovery. Current Opinion in Biotechnology 30:230-237.
132. Matos D A, Whitney I P, Harrington M J, Hazen S P. (2013) Cell walls and the developmental anatomy of the *Brachypodium distachyon* stem internode. PLoS ONE 8:e80640.
133. Nascimento F X, Rossi M J, Soares C R F S, McConkey B J, Glick B R. (2014) New insights into 1-aminocyclopropane-1-carboxylate (ACC) deaminase phylogeny, evolution and ecological significance. PLoS ONE 9:e99168.
134. Nautiyal C S. (1999) An efficient microbiological growth medium for screening phosphate solubilizing microorganisms. FEMS Microbiology Letters 170:265-270.
135. Olle B. (2013) Medicines from microbiota. Nat Biotech 31:309-315.
136. Passioura J B. (2006) The perils of pot experiments. Functional Plant Biology 33:1075-1079.
137. Penrose D, Glick B. (2003) Methods for isolating and characterizing ACC deaminase-containing plant growth-promoting rhizobacteria. Physiol Plantarum 118:10-15.
138. Pérez-García A, Romero D, de Vicente A. (2011) Plant protection and growth stimulation by microorganisms: biotechnological applications of Bacilli in agriculture. Current Opinion in Biotechnology 22:187-193.
139. Poorter H, Bühler J, van Dusschoten D, Climent J, Postma J A. (2012) Pot size matters: a meta-analysis of the effects of rooting volume on plant growth. Functional Plant Biology 39:839-850.
140. Priest H D, Fox S E, Rowley E R, Murray J R, Michael T P, Mockler T C. (2014) Analysis of global gene expression in *Brachypodium distachyon* reveals extensive network plasticity in response to abiotic stress. PLoS ONE 9:e87499.
141. Raghavan G S V, McKyes E, Taylor F, Richard P, Watson A. (1979) The relationship between machinery traffic and corn yield reductions in successive years. Transactions of the ASAE 22:1256-1259.
142. Rancour D, Marita J, Hatfield R D. (2012) Cell wall composition throughout development for the model grass *Brachypodium distanchyon*. Frontiers in Plant Science 3:e266.
143. Raus M, Sabela M. (2013) BIOSPEAN: A Freeware Tool for Processing Spectra from MALDI Intact Cell/Spore Mass Spectrometry. Journal of Proteomics & Bioinformatics 6:283-287.
144. Reisch M S. (2014) Growing profits with microbes. Chemical & Engineering News 92:23-25.
145. Research G V. 2015 Biofertilizers market analysis by product (nitrogen fixing, phosphate solubilizing), by application (seed treatment, soil Treatment) and segment forecasts to 2022. Periodical. Available from: http://www.grandviewresearch.com/industry-analysis/biofertilizers-industry.
146. Rettedal E A, Gumpert H, Sommer M O A. (2014) Cultivation-based multiplex phenotyping of human gut microbiota allows targeted recovery of previously uncultured bacteria. Nat Commun 5:4714.
147. Richard C A, Hickey L T, Fletcher S, Jennings R, Chenu K, Christopher J T. (2015) High-throughput phenotyping of seminal root traits in wheat. Plant Methods 11:1-11.
148. Specialty fertilizers market worth $19,885 million by 2020. Available from: http://www.marketsandmarkets.com/PressReleases/specialty-fertilizer.asp
149. Sahoo R, Bhardwaj D, Tuteja N. (2013) Biofertilizers: a sustainable eco-friendly agricultural approach to crop improvement. Plant Acclimation to Environmental Stress: 403-432.
150. Schellenberger U, Oral J, Rosen B A, Wei J-Z, Zhu G, Xie W, et al. (2016) A selective insecticidal protein from *Pseudomonas* for controlling corn rootworms. Science 354:634-637.
151. Scheltema R A, Jankevics A, Jansen R C, Swertz M A, Breitling R. (2011) PeakML/mzMatch: A File Format, Java Library, R Library, and Tool-Chain for Mass Spectrometry Data Analysis. Anal Chem 83.
152. Schnitzer S A, Klironomos J N, HilleRisLambers J, Kinkel L L, Reich P B, Xiao K, et al. (2010) Soil microbes drive the classic plant diversity-productivity pattern. Ecology 92:296-303.
153. Schoenborn L, Yates P S, Grinton B E, Hugenholtz P, Janssen P H. (2004) Liquid serial dilution is inferior to solid media for isolation of cultures representative of the phylum-level diversity of soil bacteria. Applied and Environmental Microbiology 70:4363-4366.
154. Schwyn B, Neilands J. (1987) Universal chemical assay for detection and determination of siderophore. Analytical Biochem 160:47-56.
155. Singhal N, Kumar M, Kanaujia P K, Virdi J S. (2015) MALDI-TOF mass spectrometry: An emerging technology for microbial identification and diagnosis. Frontiers in Microbiology 6:e791.
156. Staley J T, Konopka A. (1985) Measurement of in situ activities of nonphotosynthetic microorganisms in aquatic and terrestrial habitats. Annu Rev Microbiol 39:321-346.
157. Suzuki R, Shimodaira H. (2006) Pvclust: an R package for assessing the uncertainty in hierarchical clustering. Bioinformatics 22:1540-1542.
158. Thole V, Peraldi A, Worland B, Nicholson P, Doonan J H, Vain P. (2011) T-DNA mutagenesis in *Brachypodium distachyon*. Journal of Experimental Botany.
159. Trabucco G M, Matos D A, Lee S J, Saathoff A J, Priest H D, Mockler T C, et al. (2013) Functional characterization of cinnamyl alcohol dehydrogenase and caffeic acid O-methyltransferase in *Brachypodium distachyon*. BMC Biotechnology 13:1-18.
160. Trenberth K E, Dai A, van der Schrier G, Jones P D, Barichivich J, Briffa K R, et al. (2014) Global warming and changes in drought. Nature Clim Change 4:17-22.
161. Tullo A H. (2015) Mergers sweep fertilizer sector. Chemical & Engineering News 93:6.
162. Vílchez J I, Navas A, González-López J, Arcos S C, Manzanera M. (2015) Biosafety test for plant growth-promoting bacteria: proposed environmental and human safety index (EHSI) protocol. Frontiers in Microbiology 6:e1514.
163. Visi D K, D'Souza N, Ayre B G, Webber III C L, Allen M S. (2013) Investigation of the bacterial retting community of kenaf (*Hibiscus cannabinus*) under different conditions using next-generation semiconductor sequencing. Journal of Industrial Microbiology & Biotechnology 40:465-475.
164. Vogel J P, Garvin D F, Leong O M, Hayden D M. (2006) *Agrobacterium*-mediated transformation and inbred line development in the model grass *Brachypodium distachyon*. Plant Cell, Tissue and Organ Culture 84:199-211.
165. Waltz E. (2013) Monsanto buys microbes. Nat Biotech 31:270-270.
166. Whitlock D R. 2010 Compositions including ammonia oxidizing bacteria to increase production of nitric oxide and nitric oxide precursors and methods of using same. U.S. Pat. No. 7,820,420.
167. Wigley P, George C, Turner S. (2016) Accelerated directed evolution of microbial consortia for the development of desirable plant phenotypic traits. Patents U.S. Pat. No. 9,260,713.
168. Williams S C P. (2014) Gnotobiotics. Proceedings of the National Academy of Sciences 111:1661.
169. Wong J W H, Cagney G, Cartwright H M. (2005) SpecAlign—processing and alignment of mass spectra datasets. Bioinformatics 21:2088-2090.
170. Wong K. 2015 A new start-up hopes to develop faster-growing crops—without genetic modification. Periodical 11: [Available from: http://modernfarmer.com/2015/11/bioconsortia-increased-crop-yield/.
171. Yong X, Zhang R, Zhang N, Chen Y, Huang X, Zhao J, et al. (2013) Development of a specific real-time PCR assay targeting the poly-γ-glutamic acid synthesis gene, pgsB, for the quantification of *Bacillus amyloliquefaciens* in solid-state fermentation. Bioresource Technology 129: 477-484.
172. Yordem B K, Conte S S, Ma J F, Yokosho K, Vasques K A, Gopalsamy S N, et al. (2011) *Brachypodium distachyon* as a new model system for understanding iron homeostasis in grasses: phylogenetic and expression analysis of Yellow Stripe-Like (YSL) transporters. Annals of Botany 108:821-833.

The invention claimed is:

1. A method of isolating one or more plant growth-promoting rhizobacteria (PGPR) from an environmental sample, the method comprising:
    a) contacting an inoculum comprising the environmental sample with a surface-sterilized seed, wherein the environmental sample is obtained from the rhizosphere, rhizoplane, or endosphere of a plant, and wherein the environmental sample comprises diverse PGPR;
    b) propagating the surface-sterilized seed in a gnotobiotic rhizobacterial isolation plant system (GRIPS), wherein the GRIPS produces a simplified model plant microbiome having controllable microbial diversity; and
    c) isolating PGPR from the GRIPS.

2. The method of claim 1, wherein the GRIPS comprises a growth medium that has been sterilized by autoclaving, fumigation, or exposure to gamma radiation.

3. The method of claim 2, wherein the growth medium comprises soil.

4. The method of claim 3, wherein the soil is field soil or artificial soil.

5. The method of claim 3, wherein the growth medium further comprises sand.

6. The method of claim 2, wherein the growth medium is maintained in round-bottom or cylindrical glass tube.

7. The method of claim 1, wherein the is PGPR are selected from the group consisting of unclassified Bacilli, *Naxibacter, Bacillus*, unclassified Geobacilli, *Tumebacillus, Paenibacillus, Chitinophaga, Methylobacterium*, and *Sphingopyxis*.

8. The method of claim 7, wherein the bacterium is a *Bacillus*.

9. The method of claim 1, wherein the surface of the seed has been sterilized by contacting the surface with ethanol.

10. The method of claim 1, wherein the inoculum comprises a serial dilution of the environmental sample sufficient to permit inoculation of the seed with the PGPR.

11. The method of claim 1, wherein the inoculum comprises soil and water.

12. The method of claim 1, wherein the inoculum is obtained by mixing soil comprising a homogeneous or heterogeneous population of rhizobacteria and water to form a suspension.

13. The method of claim 12, the method further comprising diluting the suspension.

14. The method of claim 13, wherein the suspension is diluted by a factor of from 10 to 100,000.

15. The method of claim 1, the method further comprising exposing the inoculum to heat or ethanol.

16. The method of claim 2, the method further comprising adding water to the growth medium during the incubating.

17. The method of claim 2, the method further comprising contacting the growth medium with one or more antibiotics during the incubating.

18. The method of claim 2, the method further comprising contacting the growth medium with one or more selected from the group consisting of chitin, 1-aminocyclopropane-1-carboxylic acid, and insoluble phosphate.

19. The method of claim 1, the method further comprising maintaining the seedling within the GRIPS for about 2 weeks following germination of the seedling.

20. The method of claim 19, wherein the seedling is exposed to alternating light/dark cycles while maintained within the GRIPS.

21. The method of claim 1, wherein the one or more PGPR are isolated from the root of the seedling by:
    a) mixing the root with water;
    b) separating the mixture formed in step (a) by centrifugation; and
    c) inoculating a culture medium with a pellet produced in step (b).

22. The method of claim 21, the method further comprising maintaining the culture medium under conditions suitable for the growth of the one or more PGPR.

* * * * *

UNITED STATES PATENT AND TRADEMARK OFFICE
CERTIFICATE OF CORRECTION

PATENT NO. : 10,801,079 B2
APPLICATION NO. : 16/300103
DATED : October 13, 2020
INVENTOR(S) : Michael LaMontagne et al.

Page 1 of 1

It is certified that error appears in the above-identified patent and that said Letters Patent is hereby corrected as shown below:

In the Specification
In Column 1, Line 22, delete "corning" and insert -- coming --, therefor.
In Column 5, Line 15, delete "organism, the" and insert -- organism, e.g., the --, therefor.
In Column 6, Line 33, delete "En.821." and insert -- En821. --, therefor.
In Column 13, Line 65, delete "detect," and insert -- detect --, therefor.
In Column 17, Line 31, delete "Frith," and insert -- Früh, --, therefor.

In the Claims
In Column 26, Line 5, in Claim 7, delete "the is" and insert -- the --, therefor.

Signed and Sealed this
Tenth Day of August, 2021

Drew Hirshfeld
*Performing the Functions and Duties of the
Under Secretary of Commerce for Intellectual Property and
Director of the United States Patent and Trademark Office*